United States Patent
Dodson-Swenson et al.

(10) Patent No.: US 11,229,173 B2
(45) Date of Patent: Jan. 25, 2022

(54) LETTUCE VARIETY COPPER

(71) Applicant: Syngenta Crop Protection AG, Basel (CH)

(72) Inventors: Hallie Gale Dodson-Swenson, Gilroy, CA (US); Eric Votava, Fredericksburg, TX (US)

(73) Assignee: Syngenta Crop Protection AG, Basel (CH)

( * ) Notice: Subject to any disclaimer, the term of this patent is extended or adjusted under 35 U.S.C. 154(b) by 20 days.

(21) Appl. No.: 16/819,616

(22) Filed: Mar. 16, 2020

(65) Prior Publication Data

US 2021/0282349 A1    Sep. 16, 2021

(51) Int. Cl.
*A01H 5/10* (2018.01)
*A01H 6/14* (2018.01)

(52) U.S. Cl.
CPC ............. *A01H 6/1472* (2018.05); *A01H 5/10* (2013.01)

(58) Field of Classification Search
CPC ................................ A01H 5/12; A01H 6/1472
See application file for complete search history.

(56) References Cited

U.S. PATENT DOCUMENTS

2010/0083398 A1\* 4/2010 Holland .................. A01H 5/12
                                                                         800/265

OTHER PUBLICATIONS

Latham, Jonathan R., Allison K. Wilson, and Ricarda A. Steinbrecher. "The mutational consequences of plant transformation." Journal of Biomedicine and Biotechnology 2006 (2006). (Year: 2006).\*
PVP Certificate No. 200300056 issued Dec. 12, 2005.
PVP Certificate No. 200700155 issued Jun. 5, 2008.

\* cited by examiner

*Primary Examiner* — Weihua Fan
(74) *Attorney, Agent, or Firm* — Karen A. Magri

(57) ABSTRACT

The present invention provides novel lettuce cultivar Copper and plant parts, seed, and tissue culture therefrom. The invention also provides methods for producing a lettuce plant by crossing the lettuce plants of the invention with themselves or another lettuce plant. The invention also provides lettuce plants produced from such a crossing as well as plant parts, seed, and tissue culture therefrom.

31 Claims, No Drawings

LETTUCE VARIETY COPPER

FIELD OF THE INVENTION

This invention is in the field of lettuce plants.

BACKGROUND OF THE INVENTION

The present invention relates to a lettuce (*Lactuca sativa* L.) variety designated Copper.

Practically speaking, all cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke, and *chrysanthemum*. *Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

Presently, there are over one thousand known lettuce cultivars. As a crop, lettuce is grown commercially wherever environmental conditions permit the production of an economically viable yield.

Lettuce, in general, and leaf lettuce in particular, is an important and valuable vegetable crop. Thus, there is an ongoing need for improved lettuce varieties.

SUMMARY OF THE INVENTION

According to the invention, there is provided a novel lettuce cultivar designated Copper, also known as LS15588, having desirable characteristics including large head weight and size, spherical head shape, and disease resistances (Downy Mildew and Tomato Bushy Stunt Virus [TBSV]). The invention also encompasses the seeds of lettuce cultivar Copper, the plants of lettuce cultivar Copper, plant parts of the lettuce cultivar Copper (including leaves, seed, gametes), methods of producing seed from lettuce cultivar Copper, and method for producing a lettuce plant by crossing the lettuce cultivar Copper with itself or another lettuce plant, methods for producing a lettuce plant containing in its genetic material one or more transgenes, and the transgenic lettuce plants produced by that method. The invention also relates to methods for producing other lettuce plants derived from lettuce cultivar Copper and to lettuce plants, parts thereof and seed derived by the use of those methods. The present invention further relates to hybrid lettuce seeds and plants (and parts thereof including leaves) produced by crossing lettuce cultivar Copper with another lettuce plant.

In another aspect, the present invention provides regenerable cells for use in tissue culture of lettuce cultivar Copper. In embodiments, the tissue culture is capable of regenerating plants having all or essentially all of the physiological and morphological characteristics of the foregoing lettuce plant and/or of regenerating plants having the same or substantially the same genotype as the foregoing lettuce plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, the present invention provides lettuce plants regenerated from the tissue cultures of the invention.

As a further aspect, the invention provides a method of producing lettuce seed, the method comprising crossing a plant of lettuce cultivar Copper with itself or a second lettuce plant. Optionally, the method further comprises collecting the seed.

Another aspect of the invention provides methods for producing hybrids and other lettuce plants derived from lettuce cultivar Copper. Lettuce plants derived by the use of those methods are also part of the invention as well as plant parts, seed, gametes and tissue culture from such hybrid or derived lettuce plants.

In representative embodiments, a lettuce plant derived from lettuce cultivar Copper comprises cells comprising at least one set of chromosomes derived from lettuce cultivar Copper. In embodiments, a lettuce plant or population of lettuce plants derived from lettuce cultivar Copper comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from lettuce cultivar Copper, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Copper, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the lettuce plant derived from lettuce cultivar Copper is one, two, three, four, five or more breeding crosses removed from lettuce cultivar Copper.

In embodiments, a hybrid or derived plant from lettuce cultivar Copper comprises a desired added trait(s). In representative embodiments, a lettuce plant derived from lettuce cultivar Copper comprises all of the morphological and physiological characteristics of lettuce cultivar Copper (e.g., as described in Tables 1 to 18, for example, large head weight and size, spherical head shape, downy mildew resistance and/or TBSV resistance). In embodiments, the lettuce plant derived from lettuce cultivar Copper comprises essentially all of the morphological and physiological characteristics of lettuce cultivar Copper (e.g., as described in Tables 1 to 18, for example, large head weight and size, spherical head shape, downy mildew resistance and TBSV resistance), with the addition of a desired added trait(s).

The invention also relates to methods for producing a lettuce plant comprising in its genetic material one or more transgenes and to the transgenic lettuce plant produced by those methods (and progeny lettuce plants comprising the transgene). Also provided are plant parts, seed and tissue culture from such transgenic lettuce plants, optionally wherein one or more cells in the plant part, seed, or tissue culture comprises the transgene. The transgene can be introduced via plant transformation and/or breeding techniques.

In another aspect, the present invention provides for single locus converted plants of lettuce cultivar Copper. Plant parts, seed, and tissue culture from such single locus converted plants are also contemplated by the present invention. The single locus may be a dominant or recessive allele. In representative embodiments, the single transferred locus confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single locus may be a naturally occurring lettuce locus, a genome edited locus, a mutated locus (e.g., chemically or radiation induced), or a transgene introduced into lettuce through genetic engineering techniques.

The invention further provides methods for developing lettuce plants in a lettuce plant breeding program using plant breeding techniques including, for example, recurrent selection, backcrossing, pedigree breeding, double haploid techniques, restriction fragment length polymorphism enhanced selection, genetic marker enhanced selection and/or transformation. Seeds, lettuce plants, and parts thereof, produced by such breeding methods are also part of the invention.

The invention also provides methods of multiplication or propagation of lettuce plants of the invention, which can be accomplished using any method known in the art, for example, via vegetative propagation and/or seed.

The invention further provides a method of producing food or feed comprising (a) obtaining a lettuce plant of the invention, optionally wherein the plant has been cultivated to maturity, and (b) collecting at least one lettuce plant or part thereof (e.g., leaves) from the plant.

Additional aspects of the invention include harvested products and processed products from the lettuce plants of the invention. A harvested product can be a whole plant or any plant part, as described herein. Thus, in some embodiments, a non-limiting example of a harvested product includes a seed, a leaf and/or a stem.

In representative embodiments, a processed product includes, but is not limited to: cut, sliced, ground, pureed, dried, canned, jarred, washed, packaged, frozen and/or heated leaves and/or seeds of the lettuce plants of the invention, or any other part thereof. In embodiments, the processed product includes washed and packaged leaves (or parts thereof) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of lettuce cultivar Copper.

As a further aspect, the invention provides a plant of lettuce cultivar Copper.

As an additional aspect, the invention provides a lettuce plant, or a part thereof, having all or essentially all of the physiological and morphological characteristics of a plant of lettuce cultivar Copper.

As another aspect, the invention provides leaves and/or seed of the lettuce plants of the invention and a processed product from the leaves and/or seed of the inventive lettuce plants.

As still another aspect, the invention provides a method of producing lettuce seed, the method comprising crossing a lettuce plant of the invention with itself or a second lettuce plant. The invention also provides seed produced by this method and plants produced by growing the seed.

As yet a further aspect, the invention provides a method for producing a seed of a lettuce plant derived from lettuce cultivar Copper, the method comprising: (a) crossing a lettuce plant of lettuce cultivar Copper with a second lettuce plant; and (b) allowing seed of a lettuce plant derived from lettuce cultivar Copper to form. In embodiments, the method further comprises: (c) growing a plant from the seed derived from lettuce cultivar Copper of step (b); (d) selfing the plant grown from the lettuce seed derived from lettuce cultivar Copper or crossing it to a second lettuce plant to form additional lettuce seed derived from lettuce cultivar Copper, and (e) repeating steps (c) and (d) 0 or more times to generate further derived lettuce seed. Optionally, the method comprises: (e) repeating steps (c) and (d) one or more times (e.g., one to three, one to five, one to six, one to seven, one to ten, three to five, three to six, three to seven, three to eight or three to ten times) to generate further derived lettuce plants. As another option, the method can comprise collecting the seed. The invention also provides seed produced by these methods and plants produced by growing the seed.

As another aspect, the invention provides a method of producing lettuce leaves, the method comprising: (a) obtaining a plant of lettuce cultivar Copper, optionally wherein the plant has been cultivated to maturity; and (b) collecting leaves from the plant. The invention also provides the leaves produced by this method.

Still further, as another aspect, the invention provides a method of vegetatively propagating a plant of lettuce cultivar Copper. In a non-limiting example, the method comprises: (a) collecting tissue capable of being propagated from a plant of lettuce cultivar Copper; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into lettuce cultivar Copper, the method comprising: (a) crossing a first plant of lettuce cultivar Copper with a second lettuce plant that comprises a desired trait to produce $F_1$ progeny; (b) selecting an $F_1$ progeny that comprises the desired trait; (c) crossing the selected $F_1$ progeny with lettuce cultivar Copper to produce backcross progeny; and (d) selecting backcross progeny comprising the desired trait to produce a plant derived from lettuce cultivar Copper comprising a desired trait. In embodiments, the selected progeny comprises all or essentially all the morphological and physiological characteristics of the first plant of lettuce cultivar Copper. Optionally, the method further comprises: (e) repeating steps (c) and (d) one or more times in succession (e.g., one to three, one to five, one to six, one to seven, one to ten, three to five, three to six, three to seven, three to eight or three to ten times) to produce a plant derived from lettuce cultivar Copper comprising the desired trait.

In representative embodiments, the invention also provides a method of producing a plant of lettuce cultivar Copper comprising a desired added trait, the method comprising introducing a transgene conferring the desired trait into a plant of lettuce cultivar Copper. The transgene can be introduced by transformation methods (e.g., genetic engineering) or breeding techniques. In embodiments, the plant comprising the transgene comprises all or essentially all of the morphological and physiological characteristics of lettuce cultivar Copper.

The invention also provides lettuce plants produced by the methods of the invention, wherein the lettuce plant has the desired added trait as well as seed from such lettuce plants.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, single locus converted plants, hybrid plants and lettuce plants derived from lettuce cultivar Copper have at least 1, 2, 3, 4, 5, 6, 7, 8, 9, 10 or more of the morphological and physiological characteristics of lettuce cultivar Copper (e.g., as described in Tables 1 to 18) in any combination, for example, large head weight and size, spherical head shape, downy mildew resistance and/or TBSV resistance, or even all or essentially all of the morphological and physiological characteristics of lettuce cultivar Copper, so that said plants are not significantly different for said traits than lettuce cultivar Copper, as determined at the 5% significance level when grown in the same environmental conditions; optionally, with the presence of one or more desired additional traits (e.g., male sterility, disease resistance, pest or insect resistance, herbicide resistance, and the like).

In embodiments, the plants of the invention have at least 1, 2, 3, 4, 5, 6, 7, 8, 9, 10 or more of the morphological and physiological characteristics of lettuce cultivar Copper (e.g., as described in Tables 1 to 18). For example, the plants of the invention can have one, two, three, four, five, or more (in any combination) or even all of the following characteristics: large head weight and size, spherical head shape, downy mildew resistance and/or TBSV resistance.

The invention also encompasses plant parts, plant material, pollen, ovules, leaves, fruit and seed from the lettuce plants of the invention. Also provided is a tissue culture of regenerable cells from the lettuce plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are lettuce plants regenerated from a tissue culture of the invention.

In still yet another aspect, the invention provides a method of determining a genetic characteristic of lettuce cultivar Copper or a progeny thereof, e.g., a method of determining a genotype of lettuce cultivar Copper or a progeny thereof using molecular genetic techniques. In embodiments, the method comprises detecting in the genome of a Copper plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel lettuce cultivar having desirable characteristics including large head weight and size, spherical head shape, and disease resistances (Downy Mildew and TBSV).

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotype of the $F_1$ hybrid.

"Big Vein virus". Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

"Bolting". The premature development of a flowering stalk, and subsequent seed, before a plant produces a food crop. Bolting is typically caused by late planting when temperatures are low enough to cause vernalization of the plants.

"*Bremia lactucae*". An Oomycete that causes downy mildew in lettuce in cooler growing regions.

"Core length". Length of the internal lettuce stem measured from the base of the cut and trimmed head to the tip of the stem.

"Corky root". A disease caused by the bacterium *Sphingomonas suberifaciens*, which causes the entire taproot to become brown, severely cracked, and non-functional.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all of the physiological and morphological characteristics". A plant having "essentially all of the physiological and morphological characteristics" (and similar phrases) means a plant having all of the physiological and morphological characteristics of lettuce cultivar Copper, except for the characteristic(s) derived from a converted locus/loci (e.g., a single converted locus), for example, introduced via backcrossing to variety Copper, a modified gene(s) resulting from genome editing techniques, an introduced transgene (i.e., introduced via genetic transformation techniques) or mutation, when both plants are grown under the same environmental conditions. In embodiments, a plant having "essentially all of the physiological and morphological characteristics" means a plant having all of the characteristics of the reference plant with the exception of five or fewer traits, 4 or fewer traits, 3 or fewer traits, 2 or fewer traits, or one trait. In embodiments, a plant having "essentially all of the physiological and morphological characteristics" (and similar phrases) optionally has large head weight and size, spherical head shape, downy mildew resistance and/or TBSV resistance.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Head diameter". Diameter of the cut and trimmed head, sliced vertically, and measured at the widest point perpendicular to the stem.

"Head height". Height of the cut and trimmed head, sliced vertically, and measured from the base of the cut stem to the cap leaf.

"Head weight". Weight of saleable lettuce head, cut and trimmed to market specifications.

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Lettuce Mosaic virus". A disease that can cause a stunted, deformed, or mottled pattern in young lettuce and yellow, twisted, and deformed leaves in older lettuce.

"Maturity date". Maturity refers to the stage when the plants are of full size and/or optimum weight and/or in marketable form to be of commercial or economic value.

"*Nasonovia ribisnigri*". A lettuce aphid that colonizes the innermost leaves of the lettuce plant, contaminating areas that cannot be treated easily with insecticides.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Quantitative Trait Loci". Quantitative Trait Loci (QTL) refers to genetic loci that control to some degree, numerically representable traits that are usually continuously distributed.

"Ratio of head height/diameter". Head height divided by the head diameter is an indication of the head shape; <1 is flattened, 1=round, and >1 is pointed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A lettuce plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus converted". A single locus converted or conversion plant refers to a plant that is developed by plant breeding techniques (e.g., backcrossing), genome editing techniques, genetic transformation techniques and/or mutation techniques wherein essentially all of the desired morphological and physiological characteristics of a line are recovered in addition to the single locus introduced into the line via the plant breeding, genome editing, genetic transformation, or mutation techniques.

"Substantially equivalent characteristic". A characteristic that, when compared, does not show a statistically significant difference (e.g., p=0.05) from the mean.

"Tip burn". Means a browning of the edges or tips of lettuce leaves that is a physiological response to a lack of calcium.

"Tomato Bushy Stunt". Also called "lettuce necrotic stunt". A disease that causes stunting of growth and leaf mottling.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Botanical Description of the Lettuce Cultivar Copper (LS15588).

Characteristics. Lettuce variety Copper (LS15588) is an iceberg lettuce variety suitable for production in the southwest deserts of California and Arizona in spring harvesting seasons. Lettuce variety Copper resulted from a cross of iceberg lettuce varieties and several generations of individual plant selections chosen for head shape, weight, and Downy Mildew resistance.

Lettuce variety Copper has shown uniformity and stability for the traits, within the limits of environmental influence for the traits. It has been self-pollinated a sufficient number of generations with careful attention to uniformity of plant type. The variety has been increased with continued observation for uniformity. No variant traits have been observed or are expected in variety Copper.

TABLE 1

Variety Description Information

Plant Type: Iceberg
Seed

Seed color: Black
Light dormancy: Light not required
Heat dormancy: Susceptible
Cotyledon to Fourth Leaf Stage Shape of cotyledons: Spatulate
Shape of 4$^{th}$ leaf: Elongated
Apical margin: Entire
Basel margin: Coarsely Dentate
Undulation: Flat
Anthocyanin distribution: Absent
Rolling: Absent
Cupping: Slight
Reflexing: Apical Margin
Mature Leaves Margin incision depth: Moderate
Margin indentation: Shallowly dentate
Margin undulation of the apical margin: Moderate
Green color of outer leaves: Medium green
Anthocyanin distribution: Absent
Glossiness: Moderate
Leaf blistering: Moderate
Trichomes: Absent
Leaf thickness: Intermediate
Plant at Market Stage Head shape: Spherical
Head size class: Large
Head weight (g): 978
Head firmness: Very firm
Butt Shape: Rounded
Butt Midrib: Prominently raised
Core Diameter at base of head (mm): 36.5
Core height from base of head to apex (mm): 46.7
Maturity (days)

Spring: 105 to 110 days
Adaptation

Primary U.S. Regions of Adaptation (tested and proven adapted)
Southwest (California, Arizon desert): Yes
West Cost: Not adapted
Southeast: Not tested
Northeast: No tested TABLE 1-continued Variety Description Information Spring area: Yuma and Imperial (California)
Summer area: Not adapted
Fall area: Not adapted
Winter area: Not adapted
Greenhouse: Not tested
Soil type: Both of mineral and organic
Disease and Stress Reactions Virus
Tomato Bushy Stunt virus (TBSV): Highly resistant
Big vein: Not tested
Lettuce Mosaic virus: Not tested
Cucumber Mosaic virus: Not tested
Broad Bean Wilt: Not tested
Turnip Mosaic virus: Not tested
Best Western Yellows: Not tested
Lettuce Infectious Yellows: Not tested
Lettuce Mosaic Virus strain Ls-1: Susceptible
Fungal/Bacterial
*Bremia lactucae* (Downy Mildew): Highly Resistant to BI: 16-26, 2 8, 32EU, BI: 5-9US
Powdery Mildew: Not tested
Sclerontinia Rot: Not tested
Bacterial Soft Rot (Pseudomonas spp. & others): Not tested
Botrytis (Gray Mold): Not tested
Insects
Cabbage Loopers: Not tested
Nasonovia biotype WO: Highly resistant
Root Aphids: Not tested
Green Peach Aphid: Not tested
Physiological / Stress
Tip burn: Not tested
Heat: Not tested
Drought: Not tested
Cold: Intermediate
Salt: Not tested
Brown Rib: Not tested
Post-Harvest
Pink Rib: Not tested
Russett Spotting: Not tested
Rusty Brown Discoloration: Not tested
Internal Rib Necrosis (Blackheart, Gray Rib, Gray Streak): Not tested
Brown Stain: Not tested

TABLE 2

Length (mm) of 4th Leaf at 20 Days

| Copper | Navajo | Havasu |
| --- | --- | --- |
| 27 | 27 | 30 |
| 25 | 30 | 33 |
| 24 | 28 | 33 |
| 20 | 35 | 28 |
| 25 | 30 | 20 |
| 28 | 30 | 25 |
| 30 | 25 | 23 |
| 30 | 35 | 25 |
| 34 | 29 | 20 |
| 28 | 28 | 24 |
| 30 | 27 | 20 |
| 28 | 35 | 30 |
| 27 | 36 | 36 |
| 30 | 32 | 30 |
| 23 | 31 | 35 |
| 30 | 30 | 19 |
| 22 | 33 | 29 |
| 20 | 37 | 27 |
| 28 | 28 | 30 |
| 32 | 27 | 25 |

TABLE 2-continued

| ANOVA Source of Variation | Response Variable: | Length (mm) of 4th Leaf at 20 Days | | | |
| --- | --- | --- | --- | --- | --- |
| | df | SS | MS | F | P-value |
| Variety | 2 | 170.4 | 85.22 | 4.784 | 0.0120 |

| Variety | Mean | Duncan Grouping |
| --- | --- | --- |
| Navajo | 30.7 | a |
| Havasu | 27.1 | b |
| Copper | 27.1 | b |

ANOVA shows a significant difference (p < 0.05) in the length (mm) of 4th leaf at 20 days. The average length (mm) of 4th leaf for Navajo, Havasu, and Copper is 30.7, 27.1, and 27.1, respectively. However, based on the Duncan grouping, there are no differences between means for Havasu and Copper.

TABLE 3

Width (mm) of 4th Leaf at 20 Days

| Copper | Navajo | Havasu |
| --- | --- | --- |
| 13 | 13 | 17 |
| 10 | 11 | 20 |
| 9 | 12 | 21 |
| 13 | 15 | 17 |
| 14 | 14 | 11 |
| 12 | 16 | 18 |
| 15 | 15 | 19 |
| 12 | 20 | 18 |
| 18 | 17 | 16 |
| 16 | 12 | 19 |
| 10 | 18 | 15 |
| 16 | 20 | 18 |
| 12 | 18 | 24 |
| 16 | 17 | 20 |
| 10 | 19 | 20 |
| 10 | 15 | 11 |
| 10 | 13 | 18 |
| 11 | 16 | 17 |
| 12 | 12 | 20 |
| 15 | 12 | 19 |

| ANOVA Source of Variation | Response Variable: | Width (mm) of 4th Leaf at 20 Days | | | |
| --- | --- | --- | --- | --- | --- |
| | df | SS | MS | F | P-value |
| Variety | 2 | 270.4 | 135.22 | 16.76 | <0.0001 |

| Variety | Mean | Duncan Grouping |
| --- | --- | --- |
| Havasu | 17.9 | a |
| Navajo | 15.3 | b |
| Copper | 12.7 | c |

ANOVA shows a significant difference (p < 0.0001) in the width (mm) of 4th leaf at 20 days. The average width (mm) of 4th leaf for Havasu, Navajo, and Copper is 17.9, 15.3, and 12.7, respectively.

TABLE 4

Length to Width Index of 4th Leaf at 20 Days

| Copper | Navajo | Havasu |
| --- | --- | --- |
| 2.1 | 2.1 | 1.8 |
| 2.5 | 2.7 | 1.7 |
| 2.7 | 2.3 | 1.6 |
| 1.5 | 2.3 | 1.6 |
| 1.8 | 2.1 | 1.8 |
| 2.3 | 1.9 | 1.4 |
| 2.0 | 1.7 | 1.2 |

TABLE 4-continued

| | | |
|---|---|---|
| 2.5 | 1.8 | 1.4 |
| 1.9 | 1.7 | 1.3 |
| 1.8 | 2.3 | 1.3 |
| 3.0 | 1.5 | 1.3 |
| 1.8 | 1.8 | 1.7 |
| 2.3 | 2.0 | 1.5 |
| 1.9 | 1.9 | 1.5 |
| 2.3 | 1.6 | 1.8 |
| 3.0 | 2.0 | 1.7 |
| 2.2 | 2.5 | 1.6 |
| 1.8 | 2.3 | 1.6 |
| 2.3 | 2.3 | 1.5 |
| 2.1 | 2.3 | 1.3 |

| ANOVA Source of Variation | Response Variable: df | Length to Width Index of 4th Leaf at 20 Days | | |
|---|---|---|---|---|
| | | SS | MS | F | P-value |
| Variety | 2 | 4.944 | 2.472 | 23.77 | <0.0001 |

| Variety | Mean | Duncan Grouping |
|---|---|---|
| Copper | 2.18 | a |
| Navajo | 2.06 | a |
| Havasu | 1.52 | b |

ANOVA shows a significant difference ($p < 0.0001$) in the length to width index of 4th leaf at 20 days. The average length to width index of 4th leaf for Copper, Navajo, and Havasu is 2.18, 2.06, and 1.52, respectively. However, based on the Duncan grouping, there are no differences between means for Copper and Navajo.

TABLE 5

Length (mm) of Cotyledon at 20 Days

| Copper | Navajo | Havasu |
|---|---|---|
| 10 | 14 | 10 |
| 9 | 10 | 10 |
| 12 | 9 | 11 |
| 12 | 10 | 11 |
| 10 | 10 | 12 |
| 10 | 12 | 12 |
| 10 | 14 | 9 |
| 12 | 11 | 10 |
| 10 | 11 | 10 |
| 9 | 12 | 10 |
| 10 | 10 | 12 |
| 12 | 12 | 10 |
| 12 | 11 | 10 |
| 10 | 10 | 10 |
| 9 | 11 | 10 |
| 8 | 10 | 11 |
| 8 | 11 | 10 |
| 10 | 12 | 10 |
| 9 | 12 | 10 |
| 12 | 11 | 10 |

| ANOVA Source of Variation | Response Variable: df | Length (mm) of Cotyledon at 20 Days | | | |
|---|---|---|---|---|---|
| | | SS | MS | F | P-value |
| Variety | 2 | 10.03 | 5.017 | 3.55 | 0.0352 |

| Variety | Mean | Duncan Grouping |
|---|---|---|
| Navajo | 11.2 | a |
| Havasu | 10.4 | ab |
| Copper | 10.2 | b |

ANOVA shows a significant difference ($p < 0.05$) in the length (mm) of the cotyledon at 20 days. The average length (mm) of the cotyledon for Navajo, Havasu, and Copper is 11.2, 10.4, and 10.2, respectively. However, based on the Duncan grouping, there are no differences between means for Navajo and Havasu or between Havasu and Copper.

TABLE 6

Width (mm) of Cotyledon at 20 Days

| Copper | Navajo | Havasu |
|---|---|---|
| 8 | 8 | 9 |
| 7 | 8 | 10 |
| 10 | 7 | 10 |
| 9 | 8 | 9 |
| 8 | 8 | 10 |
| 7 | 8 | 9 |
| 9 | 9 | 7 |
| 11 | 8 | 10 |
| 6 | 8 | 9 |
| 8 | 9 | 10 |
| 10 | 7 | 11 |
| 10 | 10 | 10 |
| 11 | 8 | 9 |
| 9 | 8 | 10 |
| 7 | 9 | 9 |
| 6 | 7 | 10 |
| 8 | 8 | 9 |
| 7 | 9 | 9 |
| 8 | 8 | 10 |
| 10 | 8 | 10 |

| ANOVA Source of Variation | Response Variable: df | Width (mm) of Cotyledon at 20 Days | | | |
|---|---|---|---|---|---|
| | | SS | MS | F | P-value |
| Variety | 2 | 20.1 | 10.05 | 8.363 | 0.0006 |

| Variety | Mean | Duncan Grouping |
|---|---|---|
| Havasu | 9.5 | a |
| Copper | 8.5 | b |
| Navajo | 8.2 | b |

ANOVA shows a significant difference ($p < 0.001$) in the width (mm) of the cotyledon at 20 days. The average width (mm) of the cotyledon for Havasu, Copper, and Navajo is 9.5, 8.5, and 8.2, respectively. However, based on the Duncan grouping, there are no differences between means for Copper and Navajo.

TABLE 7

Length to Width Index of Cotyledon at 20 Days

| Copper | Navajo | Havasu |
|---|---|---|
| 1.3 | 1.8 | 1.1 |
| 1.3 | 1.3 | 1.0 |
| 1.2 | 1.3 | 1.1 |
| 1.3 | 1.3 | 1.2 |
| 1.3 | 1.3 | 1.2 |
| 1.4 | 1.5 | 1.3 |
| 1.1 | 1.6 | 1.3 |
| 1.1 | 1.4 | 1.0 |
| 1.7 | 1.4 | 1.1 |
| 1.1 | 1.3 | 1.0 |
| 1.0 | 1.4 | 1.0 |
| 1.2 | 1.2 | 1.0 |
| 1.1 | 1.4 | 1.1 |
| 1.1 | 1.3 | 1.0 |
| 1.3 | 1.2 | 1.1 |
| 1.3 | 1.4 | 1.1 |
| 1.0 | 1.4 | 1.1 |
| 1.4 | 1.3 | 1.1 |

-continued
TABLE 7

| | 1.1 | | 1.5 | 1.0 |
| | 1.2 | | 1.4 | 1.0 |
| ANOVA Source of Variation | Response Variable: | Length to Width Index of Cotyledon at 20 Days | | |
| | df | SS | MS | F | P-value |
| Variety | 2 | 0.7338 | 0.3669 | 20.55 | <0.0001 |

-continued
TABLE 7

| Variety | Mean | Duncan Grouping |
|---|---|---|
| Navajo | 1.4 | a |
| Copper | 1.2 | b |
| Havasu | 1.1 | c |

ANOVA shows a significant difference ($p < 0.0001$) in the length to width index of the cotyledon at 20 days. The average length to width index of the cotyledon for Navajo, Copper, and Havasu is 1.4, 1.2, and 1.1, respectively.

TABLE 8

Head Weight (g) at Harvest Maturity

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 1079 | 840 | 919 | 1132 | 642 | 846 | 856 | 626 | 728 |
| 716 | 907 | 851 | 712 | 845 | 1004 | 1062 | 277 | 693 |
| 1140 | 744 | 960 | 815 | 790 | 1006 | 953 | 330 | 538 |
| 1152 | 713 | 704 | 962 | 926 | 1321 | 784 | 491 | 631 |
| 1217 | 779 | 776 | 799 | 1088 | 1028 | 855 | 330 | 721 |
| 1087 | 833 | 487 | 732 | 1076 | 641 | 663 | 433 | 460 |
| 1111 | 727 | 618 | 906 | 790 | 1154 | 742 | 450 | 636 |
| 1092 | 1107 | 646 | 838 | 907 | 597 | 988 | 290 | 742 |
| 940 | 1074 | 692 | 629 | 876 | 1242 | 806 | 205 | 576 |
| 1177 | 956 | 553 | 819 | 743 | 885 | 934 | 400 | 632 |
| 1199 | 954 | 451 | | | | | | |
| 871 | 470 | 703 | | | | | | |
| 1149 | 645 | 691 | | | | | | |
| 1147 | 1027 | 772 | | | | | | |
| 1170 | 1059 | 569 | | | | | | |
| 1238 | 1180 | 827 | | | | | | |
| 1125 | 576 | 640 | | | | | | |
| 1214 | 911 | 708 | | | | | | |
| 1221 | 658 | 751 | | | | | | |
| 1103 | 468 | 496 | | | | | | |

ANOVA Response Variable: Head Weight (g) at Harvest Maturity

| Source of Variation | df | SS | MS | F | P-value |
|---|---|---|---|---|---|
| Variety | 2 | 1548193 | 774097 | 31.77 | <0.0001 |
| Location | 2 | 1454326 | 727163 | 29.84 | <0.0001 |
| Variety: Location | 4 | 1510888 | 377722 | 15.50 | <0.0001 |

| Variety | Mean | Duncan Grouping |
|---|---|---|
| Copper | 978.4 | a |
| Havasu | 747.4 | b |
| Navajo | 728.6 | b |

ANOVA shows a significant difference ($p < 0.0001$) of head weight (g) at harvest maturity stage for variety, location, and in the interaction between variety and location. The average head weight (g) for Copper, Havasu, and Navajo is 978.4, 747.4, and 728.6, respectively. However, based on the Duncan grouping, there are no differences between means for Havasu and Navajo.

TABLE 9

Head circumference (cm) at Harvest Maturity

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 52.0 | 53.0 | 44.0 | 45.0 | 43.0 | 52.7 | 51.0 | 43.3 | 45.4 |
| 52.0 | 48.0 | 50.0 | 42.0 | 51.7 | 56.0 | 54.9 | 38.0 | 47.3 |
| 53.0 | 46.0 | 45.0 | 45.7 | 51.6 | 57.9 | 53.0 | 44.6 | 49.4 |
| 51.0 | 49.0 | 44.0 | 51.0 | 48.4 | 52.9 | 49.5 | 44.9 | 42.6 |
| 53.0 | 50.0 | 44.0 | 49.0 | 47.0 | 50.2 | 52.0 | 44.8 | 43.4 |
| 51.0 | 47.0 | 45.0 | 46.3 | 45.9 | 50.0 | 49.6 | 41.9 | 50.2 |
| 50.0 | 48.0 | 44.0 | 44.8 | 47.8 | 54.0 | 47.9 | 47.5 | 47.9 |
| 50.0 | 44.0 | 46.0 | 50.5 | 46.9 | 51.0 | 51.2 | 44.2 | 43.3 |
| 53.0 | 52.0 | 43.0 | 47.2 | 50.3 | 56.6 | 53.0 | 43.5 | 43.8 |

TABLE 9-continued

| | | | | | | | | |
|---|---|---|---|---|---|---|---|---|
| 48.0 | 49.0 | 48.0 | 46.4 | 44.8 | 57.5 | 52.1 | 48.8 | 45.8 |
| 52.0 | 53.0 | 47.0 | | | | | | |
| 51.0 | 50.0 | 47.0 | | | | | | |
| 51.0 | 55.0 | 45.0 | | | | | | |
| 51.0 | 50.0 | 46.0 | | | | | | |
| 50.0 | 48.0 | 46.0 | | | | | | |
| 52.0 | 53.0 | 49.0 | | | | | | |
| 52.0 | 47.0 | 48.0 | | | | | | |
| 51.0 | 51.0 | 43.0 | | | | | | |
| 52.0 | 48.0 | 47.0 | | | | | | |
| 48.0 | 50.0 | 44.0 | | | | | | |

ANOVA Response Variable: Head circumference (cm) at Harvest Maturity

| Source of Variation | df | SS | MS | F | P-value |
|---|---|---|---|---|---|
| Variety | 2 | 146.4 | 73.2 | 12.35 | <0.0001 |
| Location | 2 | 87.6 | 43.8 | 7.39 | 0.0010 |
| Variety: Location | 4 | 745.2 | 186.3 | 31.43 | <0.0001 |

| Variety | Mean | Duncan Grouping |
|---|---|---|
| Copper | 50.1 | a |
| Havasu | 47.8 | b |
| Navajo | 47.7 | b |

ANOVA shows a significant difference (p < 0.005) of head circumference (cm) at harvest maturity stage for variety, location, and in the interaction between variety and location. The average head circumference (cm) for Copper, Havasu, and Navajo is 50.1, 47.8, and 47.7, respectively. However, based on the Duncan grouping, there are no differences between means for Havasu and N avajo.

TABLE 10

Core Length (mm) from Base-Market Trimmed, Single Cap Leaf

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 45 | 45 | 25 | 50 | 43 | 40 | 59 | 42 | 39 |
| 50 | 40 | 32 | 50 | 41 | 35 | 59 | 31 | 51 |
| 45 | 41 | 40 | 45 | 37 | 41 | 54 | 29 | 42 |
| 50 | 27 | 20 | 38 | 35 | 36 | 40 | 35 | 53 |
| 40 | 42 | 39 | 33 | 33 | 37 | 40 | 35 | 41 |
| 40 | 41 | 32 | 51 | 32 | 28 | 56 | 20 | 44 |
| 34 | 39 | 36 | 35 | 30 | 37 | 51 | 38 | 48 |
| 50 | 47 | 30 | 38 | 38 | 50 | 56 | 27 | 35 |
| 44 | 48 | 38 | 34 | 31 | 24 | 57 | 29 | 41 |
| 45 | 45 | 33 | 44 | 40 | 38 | 56 | 38 | 52 |
| 48 | 47 | 38 | | | | | | |
| 51 | 44 | 40 | | | | | | |
| 50 | 42 | 40 | | | | | | |
| 43 | 37 | 34 | | | | | | |
| 50 | 41 | 27 | | | | | | |
| 47 | 47 | 34 | | | | | | |
| 50 | 50 | 40 | | | | | | |
| 45 | 33 | 35 | | | | | | |
| 45 | 38 | 30 | | | | | | |
| 51 | 28 | 35 | | | | | | |

ANOVA Response Variable: Core Length (mm) from Base-Market Trimmed

| Source of Variation | df | SS | MS | F | P-value |
|---|---|---|---|---|---|
| Variety | 2 | 2297 | 1148.6 | 32.322 | <0.0001 |
| Location | 2 | 398 | 199.1 | 5.604 | 0.0048 |
| Variety: Location | 4 | 1530 | 382.4 | 10.762 | <0.0001 |

TABLE 10-continued

| Variety | Mean | Duncan Grouping |
|---|---|---|
| Copper | 46.7 | a |
| Navajo | 37.7 | b |
| Havasu | 37.3 | b |

ANOVA shows a significant difference ($p < 0.005$) of core length (mm) from base-market trimmed, single cap leaf at harvest maturity stage for variety, location, and in the interaction between variety and location. The average core length (mm) for Copper, Navajo, and Havasu is 46.7, 37.7, and 37.3, respectively. However, based on the Duncan grouping, there are no differences between means for Navajo and Havasu.

TABLE 11

Core Diameter (mm) from Base-Market Trimmed, Single Cap Leaf

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 35 | 30 | 26 | 35 | 30 | 35 | 35 | 28 | 30 |
| 39 | 25 | 31 | 36 | 38 | 30 | 41 | 27 | 30 |
| 35 | 28 | 30 | 35 | 35 | 38 | 40 | 27 | 28 |
| 39 | 21 | 23 | 39 | 39 | 44 | 32 | 20 | 30 |
| 38 | 34 | 25 | 37 | 31 | 40 | 38 | 29 | 28 |
| 30 | 29 | 28 | 38 | 30 | 27 | 40 | 20 | 25 |
| 35 | 33 | 30 | 30 | 29 | 37 | 39 | 28 | 30 |
| 35 | 30 | 25 | 37 | 30 | 40 | 38 | 24 | 26 |
| 35 | 29 | 30 | 34 | 30 | 24 | 39 | 25 | 31 |
| 35 | 25 | 25 | 39 | 38 | 39 | 37 | 24 | 34 |
| 38 | 27 | 28 | | | | | | |
| 37 | 33 | 35 | | | | | | |
| 39 | 28 | 30 | | | | | | |
| 33 | 26 | 27 | | | | | | |
| 40 | 30 | 27 | | | | | | |
| 35 | 30 | 29 | | | | | | |
| 40 | 30 | 30 | | | | | | |
| 30 | 24 | 28 | | | | | | |
| 36 | 28 | 24 | | | | | | |
| 36 | 25 | 29 | | | | | | |

ANOVA Response Variable: Core Diameter (mm) from Base-Market Trimmed

| Source of Variation | df | SS | MS | F | P-value |
|---|---|---|---|---|---|
| Variety | 2 | 1373.6 | 686.8 | 58.09 | <0.0001 |
| Location | 2 | 368.1 | 184.0 | 15.57 | <0.0001 |
| Variety: Location | 4 | 347.5 | 86.9 | 7.35 | <0.0001 |

| Variety | Mean | Duncan Grouping |
|---|---|---|
| Copper | 36.5 | a |
| Havasu | 30.2 | b |
| Navajo | 28.7 | b |

ANOVA shows a significant difference ($p < 0.0001$) of core diameter (mm) from base-market trimmed, single cap leaf at harvest maturity stage for variety, location, and in the interaction between variety and location. The average core diameter (mm) for Copper, Havasu, and Navajo is 36.5, 30.2, and 28.7, respectively. However, based on the Duncan grouping, there are no differences between means for Havasu and Navajo.

TABLE 12

Core Length to Diameter Index (mm) from Base-Market Trimmed, Single Cap Leaf

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 1.29 | 1.50 | 0.96 | 1.43 | 1.43 | 1.14 | 1.69 | 1.50 | 1.30 |
| 1.28 | 1.60 | 1.03 | 1.39 | 1.08 | 1.17 | 1.44 | 1.15 | 1.70 |
| 1.29 | 1.46 | 1.33 | 1.29 | 1.06 | 1.08 | 1.35 | 1.07 | 1.50 |
| 1.28 | 1.29 | 0.87 | 0.97 | 0.90 | 0.82 | 1.25 | 1.75 | 1.77 |
| 1.05 | 1.24 | 1.56 | 0.89 | 1.06 | 0.93 | 1.05 | 1.21 | 1.46 |
| 1.33 | 1.41 | 1.14 | 1.34 | 1.07 | 1.04 | 1.40 | 1.00 | 1.76 |
| 0.97 | 1.18 | 1.20 | 1.17 | 1.03 | 1.00 | 1.31 | 1.36 | 1.60 |

TABLE 12-continued

| | | | | | | | | |
|---|---|---|---|---|---|---|---|---|
| 1.43 | 1.57 | 1.20 | 1.03 | 1.27 | 1.25 | 1.47 | 1.13 | 1.35 |
| 1.26 | 1.66 | 1.27 | 1.00 | 1.03 | 1.00 | 1.46 | 1.16 | 1.32 |
| 1.29 | 1.80 | 1.32 | 1.13 | 1.05 | 0.97 | 1.51 | 1.58 | 1.53 |
| 1.26 | 1.74 | 1.36 | | | | | | |
| 1.38 | 1.33 | 1.14 | | | | | | |
| 1.28 | 1.50 | 1.33 | | | | | | |
| 1.30 | 1.42 | 1.26 | | | | | | |
| 1.25 | 1.37 | 1.00 | | | | | | |
| 1.34 | 1.57 | 1.17 | | | | | | |
| 1.25 | 1.67 | 1.33 | | | | | | |
| 1.50 | 1.38 | 1.25 | | | | | | |
| 1.25 | 1.36 | 1.25 | | | | | | |
| 1.42 | 1.12 | 1.21 | | | | | | |

| ANOVA Response Variable: Core Length to Diameter Index | | | | | |
|---|---|---|---|---|---|
| Source of Variation | df | SS | MS | F | P-value |
| Variety | 2 | 0.13 | 0.064 | 2.269 | 0.1080 |
| Location | 2 | 1.51 | 0.755 | 26.802 | <0.0001 |
| Variety: Location | 4 | 0.89 | 0.222 | 7.885 | <0.0001 |

ANOVA shows a significant difference ($p < 0.0001$) of core length to core diameter from base-market trimmed, single cap leaf at harvest maturity stage for location and in the interaction between variety and location, but there was no significant difference between variety.

TABLE 13

Length of Frame Leaves (cm) at Harvest Maturity

| Copper | Navajo | Havasu | Copper | Navajo | Havasu | Copper | Navajo | Havasu |
|---|---|---|---|---|---|---|---|---|
| | Location 1 | | | Location 2 | | | Location 3 | |
| 25.0 | 21.0 | 23.0 | 24.0 | 19.0 | 25.0 | 23.6 | 29.0 | 21.7 |
| 24.0 | 23.0 | 24.0 | 23.0 | 19.0 | 26.0 | 25.8 | 23.0 | 21.2 |
| 26.0 | 23.0 | 22.0 | 22.0 | 21.0 | 21.0 | 25.6 | 22.0 | 26.0 |
| 24.0 | 21.0 | 22.0 | 19.0 | 21.0 | 21.0 | 23.4 | 19.7 | 23.2 |
| 26.0 | 23.0 | 23.0 | 26.0 | 19.0 | 23.0 | 25.7 | 21.2 | 22.3 |
| 26.0 | 23.0 | 21.0 | 21.0 | 23.0 | 21.0 | 25.5 | 22.3 | 23.0 |
| 25.0 | 20.0 | 21.0 | 24.0 | 20.0 | 21.0 | 26.4 | 19.0 | 27.9 |
| 25.0 | 21.0 | 21.0 | 24.0 | 19.0 | 19.0 | 26.8 | 20.2 | 23.6 |
| 24.0 | 24.0 | 21.0 | 21.0 | 21.0 | 20.0 | 22.6 | 22.5 | 23.4 |
| 23.0 | 21.0 | 22.0 | 17.0 | 19.0 | 25.0 | 26.6 | 21.0 | 23.1 |
| 26.0 | 23.0 | 20.0 | | | | | | |
| 22.0 | 24.0 | 19.0 | | | | | | |
| 23.0 | 23.0 | 19.0 | | | | | | |
| 24.0 | 23.0 | 21.0 | | | | | | |
| 23.0 | 24.0 | 20.0 | | | | | | |
| 22.0 | 22.0 | 23.0 | | | | | | |
| 27.0 | 23.0 | 19.0 | | | | | | |
| 24.0 | 22.0 | 22.0 | | | | | | |
| 25.0 | 23.0 | 24.0 | | | | | | |
| 24.0 | 22.0 | 24.0 | | | | | | |

| ANOVA Response Variable: Length of Frame Leaves (cm) at Harvest Maturity | | | | | |
|---|---|---|---|---|---|
| Source of Variation | df | SS | MS | F | P-value |
| Variety | 2 | 115.9 | 57.97 | 17.34 | <0.0001 |
| Location | 2 | 69.1 | 34.55 | 10.336 | <0.0001 |
| Variety: Location | 4 | 48.6 | 12.14 | 3.632 | 0.0081 |

| Variety | Mean | Duncan Grouping |
|---|---|---|
| Copper | 24.03 | a |
| Havasu | 22.21 | b |
| Navajo | 21.75 | b |

ANOVA shows a significant difference ($p < 0.01$) of length of frame leaves (cm) at harvest maturity stage for variety, location, and in the interaction between variety and location. The average length of frame leaves (cm) for Copper, Havasu, and Navajo is 24.03, 22.21, and 21.75, respectively. However, based on the Duncan grouping, there are no differences between means for Havasu and Navajo.

TABLE 14

Width of Frame Leaves (cm) at Harvest Maturity

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 22.0 | 25.0 | 28.0 | 30.0 | 28.0 | 27.0 | 25.6 | 22.2 | 28.0 |
| 27.0 | 25.0 | 27.0 | 30.0 | 23.0 | 24.0 | 30.9 | 23.0 | 21.5 |
| 25.0 | 24.0 | 27.0 | 22.0 | 30.0 | 29.0 | 31.4 | 18.0 | 26.9 |
| 21.0 | 19.0 | 26.0 | 21.0 | 30.0 | 27.0 | 27.1 | 24.9 | 27.2 |
| 23.0 | 24.0 | 31.0 | 31.0 | 27.0 | 27.0 | 29.4 | 20.7 | 21.4 |
| 25.0 | 22.0 | 25.0 | 26.0 | 25.0 | 35.0 | 28.0 | 19.9 | 27.6 |
| 27.0 | 22.0 | 24.0 | 24.0 | 25.0 | 25.0 | 25.6 | 20.6 | 24.7 |
| 20.0 | 20.0 | 31.0 | 27.0 | 23.0 | 20.0 | 27.5 | 20.0 | 27.8 |
| 23.0 | 23.0 | 24.0 | 22.0 | 29.0 | 27.0 | 22.9 | 22.4 | 27.0 |
| 19.0 | 21.0 | 25.0 | 20.0 | 26.0 | 26.0 | 24.0 | 22.0 | 30.4 |
| 26.0 | 24.0 | 25.0 | | | | | | |
| 25.0 | 27.0 | 25.0 | | | | | | |
| 22.0 | 20.0 | 26.0 | | | | | | |
| 26.0 | 20.0 | 27.0 | | | | | | |
| 25.0 | 25.0 | 23.0 | | | | | | |
| 25.0 | 32.0 | 24.0 | | | | | | |
| 23.0 | 25.0 | 23.0 | | | | | | |
| 21.0 | 22.0 | 24.0 | | | | | | |
| 25.0 | 23.0 | 28.0 | | | | | | |
| 26.0 | 26.0 | 30.0 | | | | | | |

ANOVA Response Variable: Width of Frame Leaves (cm) at Harvest Maturity

| Source of Variation | df | SS | MS | F | P-value |
|---|---|---|---|---|---|
| Variety | 2 | 134.7 | 67.35 | 8.191 | 0.0005 |
| Location | 2 | 60.3 | 30.14 | 3.666 | 0.0287 |
| Variety: Location | 4 | 161.2 | 40.31 | 4.903 | 0.0011 |

| Variety | Mean | Duncan Grouping |
|---|---|---|
| Havasu | 26.3 | a |
| Copper | 25.0 | b |
| Navajo | 23.7 | c |

ANOVA shows a significant difference ($p < 0.05$) of width of frame leaves (cm) at harvest maturity stage for variety, location, and in the interaction between variety and location. The average width of frame leaves (cm) for Havasu, Copper, and Navajo is 26.3, 25.0, and 23.7, respectively.

TABLE 15

Length to Width Index of Frame Leaves at Harvest Maturity

| Copper | Navajo | Havasu | Copper | Navajo | Havasu | Copper | Navajo | Havasu |
|---|---|---|---|---|---|---|---|---|
| Location 1 | | | Location 2 | | | Location 3 | | |
| 1.14 | 0.84 | 0.82 | 0.80 | 0.68 | 0.93 | 0.92 | 1.31 | 0.78 |
| 0.89 | 0.92 | 0.89 | 0.77 | 0.83 | 1.08 | 0.83 | 1.00 | 0.99 |
| 1.04 | 0.96 | 0.81 | 1.00 | 0.70 | 0.72 | 0.82 | 1.22 | 0.97 |
| 1.14 | 1.11 | 0.85 | 0.90 | 0.70 | 0.78 | 0.86 | 0.79 | 0.85 |
| 1.13 | 0.96 | 0.74 | 0.84 | 0.70 | 0.85 | 0.87 | 1.02 | 1.04 |
| 1.04 | 1.05 | 0.84 | 0.81 | 0.92 | 0.60 | 0.91 | 1.12 | 0.83 |
| 0.93 | 0.91 | 0.88 | 1.00 | 0.80 | 0.84 | 1.03 | 0.92 | 1.13 |
| 1.25 | 1.05 | 0.68 | 0.89 | 0.83 | 0.95 | 0.97 | 1.01 | 0.85 |
| 1.04 | 1.04 | 0.88 | 0.95 | 0.72 | 0.74 | 0.99 | 1.00 | 0.87 |
| 1.21 | 1.00 | 0.88 | 0.85 | 0.73 | 0.96 | 1.11 | 0.95 | 0.76 |
| 1.00 | 0.96 | 0.80 | | | | | | |
| 0.88 | 0.89 | 0.76 | | | | | | |
| 1.05 | 1.15 | 0.73 | | | | | | |
| 0.92 | 1.15 | 0.78 | | | | | | |
| 0.92 | 0.96 | 0.87 | | | | | | |
| 0.88 | 0.69 | 0.96 | | | | | | |
| 1.17 | 0.92 | 0.83 | | | | | | |
| 1.14 | 1.00 | 0.92 | | | | | | |
| 1.00 | 1.00 | 0.86 | | | | | | |
| 0.92 | 0.85 | 0.80 | | | | | | |

TABLE 15-continued

ANOVA Response Variable: Length to Width Index of Frame Leaves at Harvest Maturity

| Source of Variation | df | SS | MS | F | P-value |
|---|---|---|---|---|---|
| Variety | 2 | 0.291 | 0.1455 | 12.589 | <0.0001 |
| Location | 2 | 0.327 | 0.1633 | 14.131 | <0.0001 |
| Variety: Location | 4 | 0.318 | 0.0796 | 6.885 | <0.0001 |

| Variety | Mean | Duncan Grouping |
|---|---|---|
| Copper | 0.97 | a |
| Navajo | 0.93 | a |
| Havasu | 0.85 | b |

ANOVA shows a significant difference (p < 0.0001) of length to width index of frame leaves at harvest maturity stage for variety, location, and in the interaction between variety and location. The average length to width index of frame leaves for Copper, Navajo, and Havasu is 0.97, 0.93, and 0.85, respectively. However, based on the Duncan grouping, there are no differences between means for Copper and Navajo.

TABLE 16

Height (cm) of Mature Seed Stalk

| Copper | Navajo | Havasu |
|---|---|---|
| 101.60 | 114.30 | 129.54 |
| 121.92 | 109.22 | 127.00 |
| 119.38 | 106.68 | 127.00 |
| 119.38 | 104.14 | 134.62 |
| 116.84 | 116.84 | 132.08 |
| 111.76 | 119.38 | 129.54 |
| 101.60 | 121.92 | 129.54 |
| 106.68 | 109.22 | 129.54 |
| 104.14 | 114.30 | 127.00 |
| 104.14 | 106.68 | 124.46 |
| 104.14 | 111.76 | 121.92 |
| 109.22 | 109.22 | 124.46 |
| 111.76 | 109.22 | 127.00 |
| 114.30 | 106.68 | 132.08 |
| 114.30 | 111.76 | 129.54 |
| 116.84 | 104.14 | 129.54 |
| 111.76 | 114.30 | 132.08 |
| 106.68 | 109.22 | 129.54 |
| 106.68 | 106.68 | 132.08 |
| 109.22 | 111.76 | 132.08 |

| ANOVA Source of Variation | Response Variable: df | Height (cm) of Mature Seed Stalk SS | MS | F | P-value |
|---|---|---|---|---|---|
| Variety | 2 | 4460 | 2230 | 93.51 | <0.0001 |

| Variety | Mean | Duncan Grouping |
|---|---|---|
| Havasu | 129.03 | a |
| Navajo | 110.87 | b |
| Copper | 110.62 | b |

ANOVA shows a significant difference (p < 0.0001) in the height (cm) of mature seed stalk. The average height (cm) of mature seed stalk for Havasu, Navajo, and Copper is 129.03, 110.87, and 110.62, respectively. However, based on the Duncan grouping, there are no differences between means for Navajo and Copper.

TABLE 17

Spread (cm) of Mature Seed Stalk at Widest Point

| Copper | Navajo | Havasu |
|---|---|---|
| 55.88 | 38.10 | 40.64 |
| 50.80 | 50.80 | 45.72 |
| 53.34 | 43.18 | 43.18 |
| 55.88 | 43.18 | 40.64 |
| 53.34 | 43.18 | 43.18 |
| 55.88 | 40.64 | 40.64 |
| 55.88 | 45.72 | 45.72 |
| 58.42 | 48.26 | 45.72 |
| 66.04 | 53.34 | 40.64 |
| 55.88 | 45.72 | 40.64 |
| 53.34 | 48.26 | 40.64 |
| 53.34 | 38.10 | 45.72 |
| 58.42 | 40.64 | 50.80 |
| 60.96 | 43.18 | 48.26 |
| 50.80 | 48.26 | 43.18 |
| 63.50 | 48.26 | 43.18 |
| 55.88 | 40.64 | 45.72 |
| 55.88 | 45.72 | 43.18 |
| 58.42 | 45.72 | 45.72 |
| 53.34 | 48.26 | 43.18 |

| ANOVA Source of Variation | Response Variable: df | Spread (cm) of Mature Seed Stalk at Widest Point SS | MS | F | P-value |
|---|---|---|---|---|---|
| Variety | 2 | 1893.1 | 946.6 | 70.57 | <0.0001 |

| Variety | Mean | Duncan Grouping |
|---|---|---|
| Copper | 56.26 | a |
| Navajo | 44.96 | b |
| Havasu | 43.82 | b |

ANOVA shows a significant difference (p < 0.0001) in the spread (cm) of mature seed stalk at widest point. The average spread (cm) of mature seed stalk for Copper, Navajo, and Havasu is 56.26, 44.96, and 43.82, respectively. However, based on the Duncan grouping, there are no differences between means for Navajo and Havasu.

TABLE 18

Height to Spread Index of Mature Seed Stalk

| Copper | Navajo | Havasu |
|---|---|---|
| 1.82 | 3.00 | 3.19 |
| 2.40 | 2.15 | 2.78 |
| 2.24 | 2.47 | 2.94 |
| 2.14 | 2.41 | 3.31 |
| 2.19 | 2.71 | 3.06 |
| 2.00 | 2.94 | 3.19 |
| 1.82 | 2.67 | 2.83 |
| 1.83 | 2.26 | 2.83 |

TABLE 18-continued

| | | |
|---|---|---|
| 1.58 | 2.14 | 3.13 |
| 1.86 | 2.33 | 3.06 |
| 1.95 | 2.32 | 3.00 |
| 2.05 | 2.87 | 2.72 |
| 1.91 | 2.69 | 2.50 |
| 1.88 | 2.47 | 2.74 |
| 2.25 | 2.32 | 3.00 |
| 1.84 | 2.16 | 3.00 |
| 2.00 | 2.81 | 2.89 |
| 1.91 | 2.39 | 3.00 |
| 1.83 | 2.33 | 2.89 |
| 2.05 | 2.32 | 3.06 |

| ANOVA Source of Variation | Response Variable: df | Height to Spread Index of Mature Seed Stalk | | | |
|---|---|---|---|---|---|
| | | SS | MS | F | P-value |
| Variety | 2 | 9.597 | 4.798 | 98.6 | <0.0001 |

| Variety | Mean | Duncan Grouping |
|---|---|---|
| Havasu | 2.96 | a |
| Navajo | 2.49 | b |
| Copper | 1.98 | c |

ANOVA shows a significant difference ($p < 0.0001$) in the height to spread index of mature seed stalk at widest point. The average height to spread index of mature seed stalk for Havasu, Navajo, and Copper is 2.96, 2.49, and 1.98, respectively.

Tissue Culture.

Further reproduction of lettuce plants variety can occur by tissue culture and regeneration. Tissue culture of various tissues of lettuce and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having desired characteristics of lettuce cultivar Copper. Optionally, lettuce plants can be regenerated from the tissue culture of the invention comprising all or essentially all of the physiological and morphological characteristics of lettuce cultivar Copper.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a lettuce plant by crossing a first parent lettuce plant with a second parent lettuce plant wherein the first or second parent lettuce plant is a plant of lettuce cultivar Copper. Further, both first and second parent lettuce can come from lettuce cultivar Copper. Thus, any of the following exemplary methods using lettuce cultivar Copper are part of this invention: selfing, backcrosses, hybrid production, crosses to populations, double haploid production, and the like. All plants produced using lettuce cultivar Copper as at least one parent are within the scope of this invention, including those developed from lettuce plants derived from lettuce cultivar Copper. Advantageously, lettuce cultivar Copper can be used in crosses with other, different, lettuce plants to produce the first generation ($F_1$) lettuce hybrid seeds and plants with desirable characteristics. The lettuce plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with lettuce cultivar Copper in the development of further lettuce plants. One such embodiment is a method for developing lettuce cultivar Copper progeny lettuce plants in a lettuce plant breeding program comprising: obtaining a plant, or a part thereof, of lettuce cultivar Copper, utilizing said plant or plant part as a source of breeding material, and selecting a lettuce cultivar Copper progeny plant with molecular markers in common with lettuce cultivar Copper and/or with some, all or essentially all of the morphological and/or physiological characteristics of lettuce cultivar Copper (see, e.g., Tables 1 to 18). In representative embodiments, the progeny plant has at least 1, 2, 3, 4, 5, 6, 7, 8, 9, 10 or more of the morphological and physiological characteristics of lettuce cultivar Copper (e.g., as described in Tables 1 to 18, such as large head weight and size, spherical head shape, downy mildew resistance and/or TBSV resistance) or even all of the morphological and physiological characteristics of lettuce cultivar Copper so that said progeny lettuce plant is not significantly different for said traits than lettuce cultivar Copper, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of lettuce cultivar Copper progeny plants, comprising crossing lettuce cultivar Copper with another lettuce plant, thereby producing a population of lettuce plants that, on average, derives 50% of its alleles (i.e., TAC) from lettuce cultivar Copper. A plant of this population may be selected and repeatedly selfed or sibbed with a lettuce plant resulting from these successive filial generations or backcrossed to lettuce cultivar Copper. Another approach is to make double haploid plants to achieve homozygosity. One embodiment of this invention is a lettuce plant produced by these methods and that has obtained at least 50% of its alleles from lettuce cultivar Copper. In embodiments, the methods of the invention produce a population of lettuce plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from lettuce cultivar Copper, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Copper. One representative embodiment of this invention is the lettuce plant produced by the methods of the invention and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from lettuce cultivar Copper, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the invention encompasses Copper progeny plants having a combination of at least 2, 3, 4, 5, 6, 7, 8, 9, 10 or more of the characteristics as described herein for lettuce cultivar Copper, so that said progeny lettuce plant is not significantly different for said traits than lettuce cultivar Copper, as determined at the 5% significance level when grown in the same environmental conditions. Using techniques described herein and those known in the art, molecular markers may be used to identify said progeny plant as progeny of lettuce cultivar Copper. Mean trait values may be used to determine whether trait differences are significant, and optionally the traits are measured on plants grown under the same environmental conditions.

Progeny of lettuce cultivar Copper may also be characterized through their filial relationship with lettuce cultivar Copper, as for example, being within a certain number of breeding crosses of lettuce cultivar Copper. A breeding cross is a cross made to introduce new genetics into the progeny, and is distinguished from a cross, such as a self or a sib cross or a backcross to Copper as a recurrent parent, made to select among existing genetic alleles. The lower the number of breeding crosses in the pedigree, the closer the relationship between lettuce cultivar Copper and its progeny. For example, progeny produced by the methods described herein may be within 1, 2, 3, 4, 5 or more breeding crosses of lettuce cultivar Copper.

In representative embodiments, a lettuce plant derived from lettuce cultivar Copper comprises cells comprising at least one set of chromosomes derived from lettuce cultivar Copper. In embodiments, the lettuce plant or population of lettuce plants derived from lettuce cultivar Copper comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from lettuce cultivar Copper, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Copper, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the lettuce plant derived from lettuce cultivar Copper is one, two, three, four, five or more breeding crosses removed from lettuce cultivar Copper.

In representative embodiments, a plant derived from lettuce cultivar Copper is a double haploid plant, a hybrid plant or an inbred plant.

In embodiments, a hybrid or derived plant from lettuce cultivar Copper comprises a desired added trait. In representative embodiments, a lettuce plant derived from lettuce cultivar Copper comprises all of the morphological and physiological characteristics of lettuce cultivar Copper (e.g., as described in Tables 1 to 18, for example, large head weight and size, spherical head shape, downy mildew resistance and/or TBSV resistance). In embodiments, the lettuce plant derived from lettuce cultivar Copper comprises essentially all of the morphological and physiological characteristics of lettuce cultivar Copper (e.g., as described in Tables 1 to 18, for example, large head weight and size, spherical head shape, downy mildew resistance and TBSV resistance), with the addition of a desired added trait.

Those skilled in the art will appreciate that any of the traits described above with respect to plant transformation methods can be introduced into a plant of the invention (e.g., lettuce cultivar Copper and hybrid lettuce plants and other lettuce plants derived therefrom) using breeding techniques.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of the plants disclosed herein.

Genetic engineering techniques can be used (alone or in combination with breeding methods) to introduce one or more desired added traits into plant, for example, lettuce cultivar Copper or progeny or lettuce plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed lettuce plants using transformation methods as described herein to incorporate transgenes into the genetic material of the lettuce plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a lettuce plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for gene editing techniques.

Any transgene, including those exemplified above, can be introduced into the lettuce plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic lettuce line. The transgenic lettuce line can then be crossed with another (non-transgenic or transgenic) line in order to produce a new transgenic lettuce line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Locus Conversions.

When the term "lettuce plant" is used in the context of the present invention, this term also includes any locus conversions of that plant or variety. The term "locus converted plant" as used herein refers to those plants that are developed, for example, by backcrossing, genome editing, genetic transformation and/or mutation, wherein essentially all of the desired morphological and physiological characteristics of a variety are recovered in addition to the one or more loci introduced into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the locus/loci for the desired characteristic(s) is termed the "nonrecurrent" or "donor parent." This terminology refers to the fact that the nonrecurrent parent is generally used one time in the breeding e.g., backcross) protocol and therefore does not recur. The locus that is transferred can be a native gene, a mutated native gene (e.g., naturally occurring, by chemical or radiation mutagenesis, or by genome editing) or a transgene introduced by genetic engineering techniques into the plant (or ancestor thereof). The parental plant into which the locus/loci from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Lettuce Cultivar Copper.

The invention further provides a method of determining a genetic characteristic of lettuce cultivar Copper or a progeny thereof, e.g., a method of determining a genotype of lettuce cultivar Copper or a progeny thereof. In embodiments, the method comprises detecting in the genome of a Copper plant, or a progeny plant thereof, at least a first polymorphism (e.g., using nucleic acid amplification, nucleic acid sequencing and/or one or more molecular markers). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT INFORMATION

Applicants have made a deposit of at least 2500 seeds of lettuce cultivar Copper with the American Type Culture Collection (ATCC), 10801 University Boulevard, Manassas, Va., 20110-2209 U.S.A. under ATCC Deposit No PTA-126772 on Jun. 9, 2020. This deposit of lettuce variety Copper will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single locus modifications and mutations, somaclonal variants, variant individuals selected from large populations of the plants of the instant inbred and the like may be practiced within the scope of the invention.

What is claimed is:

1. A seed of lettuce cultivar Copper, a representative sample of seed having been deposited under ATCC Accession No. PTA-126772.

2. A plant of lettuce cultivar Copper, a representative sample of seed having been deposited under ATCC Accession No. PTA-126772.

3. A lettuce plant, or a part thereof, having all of the physiological and morphological characteristics of the lettuce plant of claim 2.

4. A progeny lettuce plant of the plant of claim 2 that comprises at least 50% of the alleles of the plant of claim 2, wherein the progeny lettuce plant comprises a spherical head shape, Downy Mildew resistance, and Tomato Bushy Stunt Virus resistance.

5. A seed that produces the plant of claim 4.

6. A plant part of the lettuce plant of claim 2.

7. The plant part of claim 6, wherein the plant part is a leaf, pollen, an ovule, an anther, a root, or a cell.

8. A tissue culture of regenerable cells of the plant of claim 2.

9. A lettuce plant regenerated from the tissue culture of claim 8 or a selfed progeny thereof, wherein said lettuce plant expresses all of the physiological and morphological characteristics of lettuce cultivar Copper.

10. A converted lettuce plant produced by introducing a single locus conversion into the plant of claim 2, wherein said converted lettuce plant comprises said single locus conversion and otherwise comprises all of the physiological and morphological characteristics of lettuce cultivar Copper.

11. A processed product from the plant of claim 2, wherein the processed product comprises cut, sliced, ground, pureed, dried, canned, jarred, washed, packaged, frozen and/or heated leaves.

12. A method of producing lettuce seed, the method comprising crossing the plant of claim 2 with itself or a second lettuce plant and harvesting the resulting seed.

13. A lettuce seed from a plant produced by the method of claim 12.

14. A lettuce plant, or part thereof, produced by growing the seed of claim 13.

15. A doubled haploid plant produced from the lettuce plant of claim 14.

16. A method for producing a seed of a lettuce plant derived from the plant of claim 2, the method comprising:
    (a) crossing a plant of lettuce cultivar Copper with a second lettuce plant; and
    (b) allowing seed to form;
    (c) growing a plant from the seed of step (b) to produce a plant derived from lettuce cultivar Copper;
    (d) selfing the plant of step (c) or crossing it to a second lettuce plant to form additional lettuce seed derived from lettuce cultivar Copper; and
    (e) optionally repeating steps (c) and (d) one or more times to generate further derived lettuce seed from lettuce cultivar Copper, wherein in step (c) a plant is grown from the additional lettuce seed of step (d) in place of growing a plant from the seed of step (b).

17. A seed produced by the method of claim 16, wherein the seed comprises at least 50% of the alleles of lettuce cultivar Copper and is within one breeding cross of lettuce cultivar Copper, and wherein the seed produces a lettuce plant that comprises a spherical head shape, Downy Mildew resistance, and Tomato Bushy Stunt Virus resistance.

18. A plant, or part thereof, produced by growing the seed of claim 17.

19. A method of vegetatively propagating the plant of claim 2, the method comprising:
    (a) collecting tissue capable of being propagated from a plant of lettuce cultivar Copper;
    (b) cultivating the tissue to obtain proliferated shoots;
    (c) rooting the proliferated shoots to obtain rooted plantlets; and
    (d) optionally, growing plants from the rooted plantlets.

20. A lettuce plantlet or plant obtained by the method of claim 19, wherein the lettuce plantlet or plant expresses all of the physiological and morphological characteristics of lettuce cultivar Copper.

21. A method of introducing a desired added trait into lettuce cultivar Copper, the method comprising:
    (a) crossing the plant of claim 2 with a lettuce plant that comprises a desired added trait to produce F1 progeny;
    (b) selecting an F1 progeny that comprises the desired added trait;
    (c) crossing the selected F1 progeny with lettuce cultivar Copper to produce backcross progeny;
    (d) selecting a backcross progeny comprising the desired added trait; and
    (e) optionally repeating steps (c) and (d) one or more times to produce a plant derived from lettuce cultivar Copper comprising a desired added trait and otherwise all of the physiological and morphological characteristics of lettuce cultivar Copper, wherein in step (c) the selected backcross progeny produced in step (d) is used in place of the selected F1 progeny of step (b).

22. The method of claim 21, wherein the desired added trait is male sterility, pest resistance, insect resistance, disease resistance, herbicide resistance, or any combination thereof.

23. A lettuce plant produced by the method of claim 21 or a selfed progeny thereof, wherein the lettuce plant is the backcross progeny of step (e) or a selfed progeny thereof and has the desired added trait and otherwise all of the physiological and morphological characteristics of lettuce cultivar Copper.

24. A seed that produces the plant of claim 23.

25. A method of producing a plant of lettuce cultivar Copper comprising a desired added trait, the method comprising introducing a transgene conferring the desired trait into the plant of claim 2.

26. A lettuce plant produced by the method of claim 25 or a selfed progeny thereof, wherein the lettuce plant is a transformed plant of lettuce cultivar Copper and has the desired added trait.

27. A seed of the plant of claim 26, wherein the seed produces a transformed plant of lettuce cultivar Copper that comprises the transgene and has the desired added trait.

28. A method of determining a genotype of lettuce cultivar Copper, the method comprising:
    (a) obtaining a sample of nucleic acids from the plant of claim 2; and
    (b) detecting a polymorphism in the nucleic acid sample.

29. A method of producing a lettuce leaf, the method comprising:
   (a) growing the lettuce plant according to claim 2 to produce a lettuce leaf; and
   (b) harvesting the lettuce leaf.

30. A method of producing a lettuce leaf, the method comprising:
   (a) growing the lettuce plant according to claim 23 to produce a lettuce leaf; and
   (b) harvesting the lettuce leaf.

31. A method of developing a lettuce line in a lettuce plant breeding program using plant breeding techniques, which include employing a lettuce plant, or its parts, as a source of plant breeding material, comprising:
   (a) obtaining the lettuce plant, or its parts, of claim 2 as a source of breeding material; and
   (b) applying plant breeding techniques.

\* \* \* \* \*